US00PP13315P2

(12) United States Plant Patent
Austin

(10) Patent No.: US PP13,315 P2
(45) Date of Patent: Dec. 3, 2002

(54) SHRUB ROSE PLANT NAMED 'AUSVERSE'

(75) Inventor: David C. H. Austin, Wolverhampton (GB)

(73) Assignee: David Austin Roses Limited, Albrighton (GB)

( * ) Notice: Subject to any disclaimer, the term of this patent is extended or adjusted under 35 U.S.C. 154(b) by 22 days.

(21) Appl. No.: 09/712,311

(22) Filed: Nov. 13, 2000

(51) Int. Cl.[7] ..... A01H 5/00

(52) U.S. Cl. ..... Plt./108

(58) Field of Search ..... Plt./108, 102, 141, Plt./151

*Primary Examiner*—Bruce R. Campell
*Assistant Examiner*—June Hwu
(74) *Attorney, Agent, or Firm*—Klarquist Sparkman, LLP

(57) ABSTRACT

Shrub rose plant that is disease resistant, having rich, dark crimson blooms that turn to a shade of rich purple and have a powerful, old rose fragrance that repeat flowers throughout the summer and has a strong, bushy, rather upright growth.

1 Drawing Sheet

LATIN NAME OF GENUS AND SPECIES

*Rosa hybrida.*

VARIETY DENOMINATION

'AUSverse'.

SUMMARY OF THE INVENTION

The present invention relates to a new and distinct shrub rose plant which was originated by me by crossing two unnamed seedlings.

BACKGROUND OF THE INVENTION

The primary objective of this breeding was to produce a new rose variety that is a disease-resistant, rich, dark crimson red rose with beautiful, full-petalled blooms with a powerful, old rose fragrance, that repeat flowers throughout the summer.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Rick, dark crimson blooms that turn to a shade of rich purple;
2. Strong, bushy rather upright growth;
3. Repeat flowering; and
4. Very good disease resistance.

Asexual reproduction of this new variety by budding, as performed at Wolverhampton, England, shows that the foregoing and all other characteristics and distinctions come true to form and are established and transmitted through succeeding propagations.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart, except where ordinary dictionary significance of color is indicated.

Parentage:
*Seed parent.*—Unnamed Seedling (unpatented).
*Pollen parent.*—Unnamed Seedling (unpatented).
Classification:
*Botanical.*—*Rosa hybrida.*
*Commercial.*—Shrub.

FLOWER

Observations made from specimens grown in a garden environment at Wolverhampton, England in July, 1998, at two years of age. The daily temperature in Wolverhampton ranges from on average a high in the mid-forties (F) and lows in the low thirties in the winter months to highs in the high sixties and lows near fifty in the summer months. Average monthly duration of bright sunshine ranges from about 180 hours in the summer months to about 50 hours in the winter months.

Blooming habit: Recurrent.
Bud:
*Size.*—About ¾ to 1 inch long when the petals start to unfurl.
*Form.*—The bud form is medium, broad based.
*Color.*—When sepals first divide, bud color is Red-Purple Group 59A. When half blown, the upper sides of the petals are Red-Purple Group 71B; and the lower sides of the petals are Red-Purple Group 70B.
*Sepals.*—Color: Yellow-Green Group 144A. Length: 1 inch. Width: ⅓ inch at the widest point. Lower surface texture: Smooth. Upper surface texture: Pubescence. There are three normally appendaged sepals with hairy edges. There are two unappendaged sepals with hairy edges.

*Receptacle.*—Color: Yellow-Green Group 144A. Shape: Funnel. Size: Medium, about ½ inch×½ inch. Surface: Smooth.

*Peduncle.*—Length: Medium, averaging about 3–3½ inches. Surface: Smooth. Color: Bronzy — Yellow-Green Group 146B with Greyed-Purple Group 185B overlay. Strength: Medium.

Bloom:

*Size.*—Medium. Average open size is 3–3½ inches.

*Borne.*—Singly and several together in clusters of up to four blooms having a rounded shape.

*Stems.*—Strength: Normal. Average length is about 24–28 inches.

*Form.*—When first open: Cupped. Permanence: Outer petals curl back.

*Petalage.*—Number of petals under normal conditions: 105.

*Color.*—The upper sides of the petals are Red-Purple Group 64B. The reverse sides of the petals are Red-Purple Group 71D. The base of each petal has Yellow Group 3C. The major color on the upper side is Red-Purple Group 61A.

*Variegations.*—None observed.

*Discoloration.*—The general tonality at the end of the first day: Paling to Red-Purple Group 64A. At the end of the third day: Becomes more purple as bloom ages.

*Fragrance: Strong, old rose.*

Petals:

*Texture.*—Average.

*Shape.*—Round, pointed at base.

*Form.*—Tips slightly recurved.

*Arrangement.*—Irregular. Petaloids in the center are few and small.

*Persistence.*—Petals hang on and dry.

*Lastingness.*—On the plant: Long (about 7 days). As a cut flower: Not tested.

Reproductive parts:

*Anthers.*—Size: Medium. Quantity: Few-average. Color: Yellow Group 12B. Arrangement: Regular around styles, a few mixed with petaloids.

*Filaments.*—Color: Yellow Group 2C.

*Pollen.*—Color: Yellow-Orange Group 15B.

*Styles.*—Color: Yellow-Green Group 150D.

*Stigmas.*—Color: Yellow-Orange Group 15C.

*Hips.*—None produced.

Plant:

*Form.*—Large shrub, English.

*Growth.*—Vigorous, rather upright, bushy. At maturity, height is 6 feet, width is 4 feet.

Foliage: Number of leaflets on normal mid-stem leaves: 5.

*Size.*—Medium (6 inches long×5 inches wide).

*Quantity.*—Normal.

*Color.*—New foliage: Upper surface: Yellow-Green Group 146B with Greyed-Purple Group 183A edge. Lower surface: Yellow-Green Group 146C with Greyed-Purple Group 183A blush. Old foliage: Upper surface: Yellow-Green Group 147A. Lower surface: Yellow-Green Group 147B.

Leaflets:

*Shape.*—Elliptic.

*Texture.*—Upper side: Leathery, semi-glossy. Under side: Matt.

*Edge.*—Serrated.

*Serration.*—Double, medium.

*Petiole rachis.*—Color: Yellow-Green Group 144C.

*Petiole underside.*—With Prickles.

*Stipules.*—Medium, serrated (about ¾ inches). Color: Green Group 143A.

*Disease resistance.*—Resistant to mildew, blackspot, and rust under normal growing conditions.

Wood:

*New wood.*—Color: Green Group 143A and Greyed-Purple Group 183A overlay. Bark: Smooth.

*Old wood.*—Color: Yellow-Green Group 146B. Bark: Smooth.

Prickles:

*Quantity.*—On main canes from base: Ordinary. On laterals from main canes: Ordinary.

*Position.*—Quite evenly distributed up the stem.

*Form.*—Medium, straight.

*Color when young.*—Greyed-Purple Group 183C with Yellow Green Group 144B undertones.

*Color when mature.*—Greyed-Orange Group 166A.

*Length.*—Young and mature are ⅓ inch.

Small prickles:

*Quantity.*—On main stalks: Few. On laterals: Few.

*Color.*—Greyed-Purple Group 183C.

Hardiness: Winter hardy to Zone 4.

I claim:

1. A new and distinct variety of rose plant of the *rosa hybrida* class, substantially as herein shown and described, characterized particularly by its rich, dark crimson blooms that turn to a shade of rich purple, with a powerful, old rose fragrance; strong, bushy rather upright growth; repeat flowering; and very good disease resistance.

* * * * *

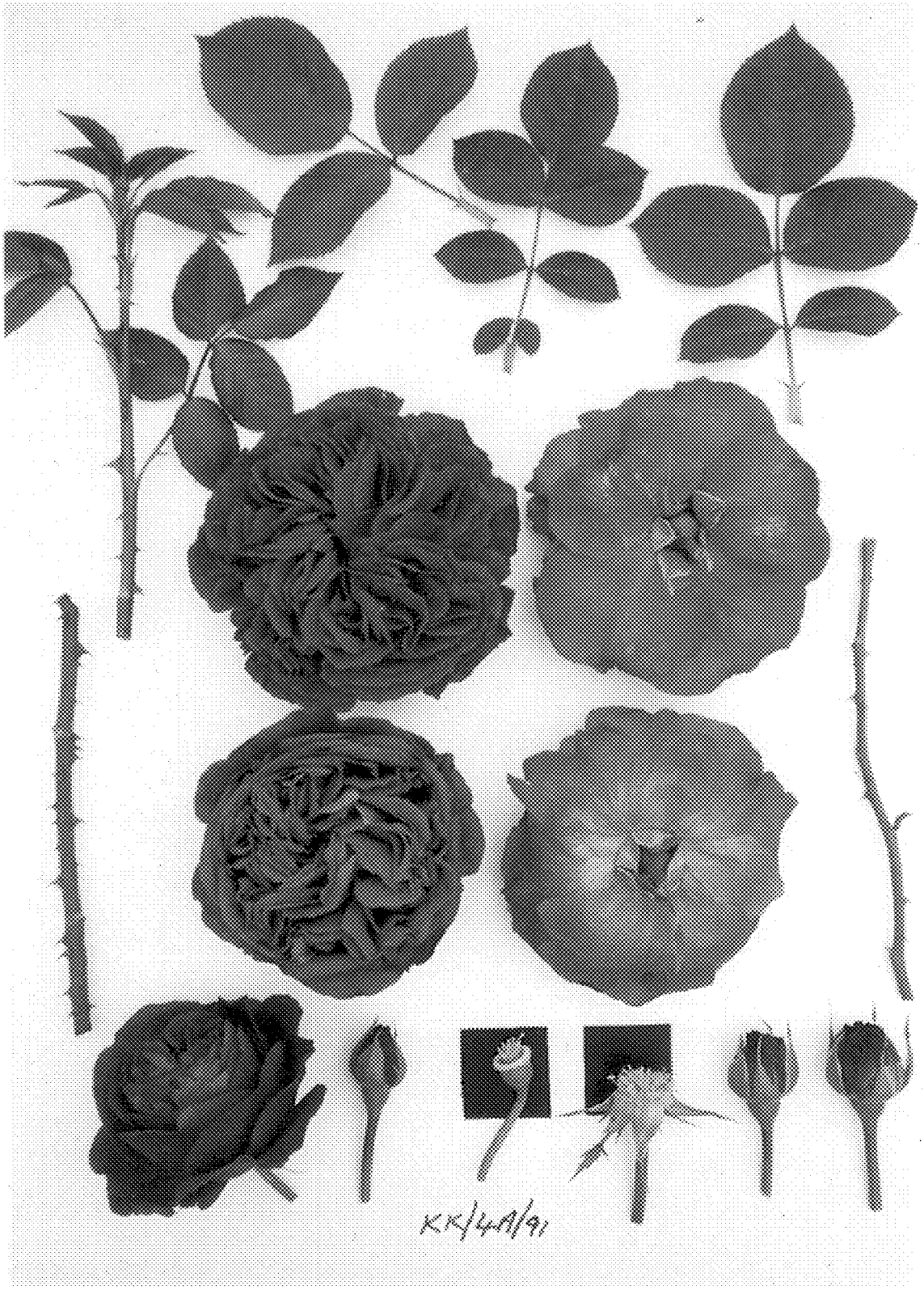
KK/4A/91